United States Patent
Rinman (10) Patent No.: US 7,125,377 B2
(45) Date of Patent: Oct. 24, 2006

(54) VALVE ASSEMBLY

(75) Inventor: Åse Rinman, Lejonslättsgatan (SE)

(73) Assignee: Eutech Medical AB, Gothenburg (SE)

( * ) Notice: Subject to any disclaimer, the term of this patent is extended or adjusted under 35 U.S.C. 154(b) by 0 days.

(21) Appl. No.: 10/626,038

(22) Filed: Jul. 24, 2003

(65) Prior Publication Data

US 2005/0177021 A1    Aug. 11, 2005

(30) Foreign Application Priority Data

Jan. 29, 2001  (SE)  .................... 0100256
Jan. 29, 2001  (SE)  .................... 0100257

(51) Int. Cl.
  *A61F 2/00*       (2006.01)
(52) U.S. Cl. ....................................... 600/29
(58) Field of Classification Search ............ 600/29–31,
   600/141, 143; 604/9, 245–247, 101.05, 103.03,
   604/269, 530, 104, 107, 349, 350; 128/885,
   128/DIG. 25; 137/854, 469, 506, 513, 614.12;
   251/65; 606/198
  See application file for complete search history.

(56) References Cited

U.S. PATENT DOCUMENTS

| | | | |
|---|---|---|---|
| 3,812,841 A * | 5/1974 | Isaacson ..................... 600/29 |
| 4,679,546 A | 7/1987 | van Waalwijk van Doorn et al. |
| 4,904,236 A * | 2/1990 | Redmond et al. .............. 604/9 |
| 5,140,999 A * | 8/1992 | Ardito ........................ 128/885 |
| 5,476,434 A * | 12/1995 | Kalb et al. .................... 600/30 |
| 5,513,659 A * | 5/1996 | Buuck et al. ............... 128/885 |
| 5,704,353 A * | 1/1998 | Kalb et al. .................. 600/342 |
| 5,885,258 A * | 3/1999 | Sachdeva et al. .......... 604/530 |
| 6,022,312 A * | 2/2000 | Chaussy et al. .............. 600/29 |
| 6,105,580 A * | 8/2000 | Von Iderstein et al. ..... 128/885 |
| 6,183,413 B1 * | 2/2001 | Migachyov .................. 600/29 |
| 6,193,646 B1 * | 2/2001 | Kulisz et al. ................. 600/29 |
| 6,237,623 B1 * | 5/2001 | Kulisz et al. ............... 137/469 |

FOREIGN PATENT DOCUMENTS

| | | |
|---|---|---|
| EP | 0 535 778 A1 | 6/1992 |
| FR | 2 767 673 | 8/1997 |
| WO | WO 00/15140 | 3/2000 |

* cited by examiner

*Primary Examiner*—Samuel Gilbert
(74) *Attorney, Agent, or Firm*—Gauthier & Connors LLP (57) ABSTRACT

The present invention relates to a valve assembly adapted to be positioned into a urethra in a mammal, including humans, the valve assembly comprising a) a valve holder and b) a valve housing comprising a valve controlling an urine flow from a patient's bladder, the valve assembly being arranged in a sealed manner between the walls of the urethra, said valve holder comprises a cylindrically shaped body to be inserted into the urethra.

31 Claims, 4 Drawing Sheets

VALVE ASSEMBLY

TECHNICAL FIELD

The present invention relates to a valve assembly intended for positioning in the urethra or similar of a patient, preferably in the upper part of the urethra, which valve assembly exhibits means for emptying the patient's urine bladder or similar through the valve assembly, as well as a valve to be positioned in said valve assembly, in particular a valve assembly adapted to be positioned into a urethra in a mammal, including humans, the valve assembly comprising a) a valve holder comprising a substantially cylindrically shaped body to be inserted into the urethra and b) a valve housing comprising a valve controlling an urine flow from a patients bladder, the valve assembly being arranged in a sealed manner between the walls of the urethra.

BACKGROUND OF THE INVENTION

Involuntary leakage of urine is a very common disorder. Urinary incontinence is not life threatening but it has a strong negative influence on Quality of Life.

About 10% of the population, mostly children and elderly people, have an insufficient control of their urinary bladder. The great majority of these have a minor degree of incontinence allowing them to lead a good life with the aid of simple measures such as a small incontinence pad or frequent change of underwear. The rest, about 1-% of the population, have a more severe incontinence that poses a serious social problem. Young people who are physically impaired regard the incontinence as a more severe handicap than the inability to walk. The urinary incontinence is considered to be the most serious obstacle for the creation of lasting relationship to other people, for their ability to live an independent, life, and for their adaptation to the society both on the private and the professional level.

Congenital malformations of the bladder or the nerves to the bladder (e.g. myelomeningocele) or traffic accidents with injury, to the spinal cord, or pelvic floor damage at childbirth, or infections of the nervous system (such as encephalitis or meningitis) cause the more serious forms of urinary incontinence. Furthermore, several of the diseases of old age, such as prostate hyperplasia of Parkinson's disease, may cause urinary, incontinence.

Generally, urinary incontinence is caused either by involuntary contractions of the bladder muscle (so called unstable bladder), or by insufficient contraction of the urethra sphincter muscle. Unstable bladder can be treated with medication or bladder training with good results. The situation is more problematic when the incontinence is due to a weak or damaged sphincter muscle. So far, there is no medication available that can increase the contraction of the sphincter without giving at the same time unacceptable side effects. The only efficient treatment today for severe cases is operation whereby an artificial sphincter is implanted around the bladder neck or urethra, controlled by the patient via an implanted pump system. This is major surgery, the cost is high (in, Sweden at least ,SK 100 000), the operation is unsuccessful in 15–25% of patients, and the device has a limited life span, meaning that reoperations will have to be performed in order to exchange components that have broken down. Therefore, many patients choose to keep their severe incontinence instead of going through a major operation with uncertain prospects.

Less than $\frac{1}{1000}$ of the population have urinary incontinence due to a faulty sphincter muscle, the most severe and therapy-resistant form of incontinence. Still, this kind of incontinence is found in millions of patients on a global scale.

Since many years, the medical profession has been searching for alternative ways to treat patients with an incompetent sphincter muscle. Some centre (Munchen, San Francisco) tries esoteric and costly methods, such as transplantation of muscle or implantation of electrostimulators. Plugs or valves have been developed (e.g., U.S. Pat. Nos. 4,679,546 and 4,643,169) for implantation in the urethra, but previously used methods and materials have caused urinary stone and infection, so these devices have been abandoned. However, the development of biocompatible materials during recent years has improved the chances for prolonged survival of an artificial valve within the urinary tract.

SE-C-504 276 relates to a valve to be inserted into the urethra, which valve comprises a valve body formed by a permanent magnet, a stop and radially extending drainage holes placed in the middle of a surrounding valve housing, whereby the valve housing is present in a fastening means consisting of an expandable material, which, is expandable by means of a liquid introduced into said expandable material.

WO 00/33766 discloses a valve for bladder control comprising an elongate housing having a proximal end and a distal end and a lumen extending therethrough, a spring actuated valve stopper, and a valve seat onto which the stopper acts to prevent flow through the valve.

U.S. Pat. No. 3,812,841 relates to a urethra magnetic valve structure, which is held in the urethra by means of inflatable retention collars.

EP-A-0 53S 778 relates to a urinary incontinence valve disposable in the urethra of a patient for controlling the flow of urine therethrough, which valve consists of a tubular body having a proximal end, a distal end and an outer diameter small enough, to be able to place the valve in the urethra. The valve comprises a lumen extending from the proximal to the distal ends. Further the vale comprises a valve seating said lumen and a valve member acting upon said valve seat to close and open said valve by means of an actuator rod. The proximal and distal ends have diameters larger than the remaining part of the valve body. The actuating rod is moreover arranged to be placed within the urine bladder and be actuated upon by a abdominal pressure. This urinary valve does not provide options for being enlarged in place in the urethra but has to be brought in place with its full diameter, which is painful and may cause damages on the urethra mucous membrane causing infections which may easily enter the urine bladder.

WO 00/15140 relates to a urinary incontinence valve comprising a proximal end and a distal end and which is adapted to fit into the neck of a bladder or the upper part of the urethra, preferably not extending to any substantial part into the urethra. The proximal end may be conical to plug the bladder neck. The plug member is made of a resilient material, such as a polymer. A valve is situated in the plug member lumen. The valve as such may use shape memory alloys for opening/closing action, a hydrogel such as a polyelectrolytic gel.

U.S. Pat. No. 4,679,546 relates to an implantable shut-off device for regulating urination and consists of a titanium made conical collar provided with a cylindrical plug member into which a flow regulating valve is inserted. The collar is arranged to be placed at the urethra opening within the urine bladder and to lock the valve from being displaced from the bladder through the urethra. The implantation of such a rigid structure cannot be made through urethra but has to be made during a major surgery. The structure does not provide for a tight fitting of the valve receiving cylindrical part in the urethra but the valve structure may even get loose and enter the bladder as such causing a lot of discomfort: and inconvenience.

SUMMARY OF THE INVENTION

Therefore, the main purpose of the present invention is to develop a valve for placement in the urethra or any other emptying tube channel in humans or animals and to construct the valve so that it is well tolerated by the patient's urethra.

The valve is intended to be changed regularly, for instance every 6 months, in order to prevent the development of urinary stone and infection. Furthermore, the pressure within the device keeping the valve in adequate position within the urethra is calibrated so that: the valve is well tolerated by the mucous membrane of the urethra but at the same time allowing the entire device to be expelled out of the patient's body in case the bladder pressure would rise to dangerous levels if the opening of the valve would be impaired, thus enhancing the safety of the valve.

Said object is achieved by means of a valve assembly in accordance with the present invention, the cylindrical valve holder comprise a shape memory alloy to provide an expandable element having the possibility to expand after the insertion of said valve holder to increase its diameter at its upper end to provide a frustoconical portion, whereby the increase of the diameter of the cylinder at its upper end is more than 15% and whereby the increase of the diameter of said cylindrical valve holder is temperature dependent.

In particular the present invention allows for a non-painful insertion without risk for damages upon the sensitive mucous membranes present in the urethra. It also allows for a simple and rational expansion of the valve holder in such a way that there will be a tight and safe closure of the urethra between the valve holder and the urethra wall. As the expansion of the valve holder is temperature dependent it is easily expanded by simply flushing the valve body with warm water to allow for expansion using the memory alloy of which the valve holder is manufactured.

BRIEF DESCRIPTION OF THE DRAWINGS

The invention is described below as a number of preferred illustrative embodiments with reference to the accompanying drawings, in which

FIG. 4A shows an enlargement of a part of the tool of FIG. 4.

DETAILED DESCRIPTION OF THE INVENTION

It has now surprisingly been found possible to solve the above problems by means of the present invention encompassing a valve assembly adapted to be positioned into a urethra in a mammal, including humans, the valve assembly comprising a) a valve holder comprising a substantially cylindrically shaped body to be inserted into the urethra and b) a valve housing comprising a valve controlling an urine flow from a patients bladder, the valve assembly being arranged in a sealed manner between the walls of the urethra, which valve assembly is characterised in that the cylindrical valve holder comprise a shape memory alloy to provide an expandable element having the possibility to expand after the insertion of said valve holder to increase its diameter at its upper end to provide a frustoconical portion, whereby the increase of the diameter of the cylinder at its upper end is more than 15%, and whereby the increase of the diameter of said cylindrical valve holder is temperature dependent.

A preferred embodiment is characterised in that the, cylinder increase its diameter at its lower end.

Another preferred embodiment is characterised in that the valve assembly comprises at least two frustoconically shaped portions A preferred embodiment is characterised in that the valve assembly comprises at least two frustoconically shaped portions at one end of the cylinder.

Another preferred embodiment is characterised in that the valve assembly comprises at least two frustoconically shaped portions at one end of the cylinder as well as at least one frustoconically shaped portion at the opposite end thereof.

A preferred embodiment is characterised in that the holder and the housing are detachable from each other when inserted in the urethra.

Another preferred embodiment is characterised in that the holder and the housing are detachable from each other.

A preferred embodiment is characterised in that the valve holder includes a first portion exhibiting a frustoconical shape, a second portion being essentially cylindrical and a third portion exhibiting a frustoconical shape directed in opposite direction in relation to the first portion.

Another preferred embodiment is characterised in that the valve holder includes a first portion exhibiting at least two parts having frustoconical shape, a second portion being essentially cylindrical and a third portion exhibiting a frustoconical shape directed in opposite direction in relation to the first portion.

Another preferred embodiment is characterised in that the holder is helix shaped wire arranged onto the valve housing.

A preferred embodiment is characterised in that the holder comprise a helix shaped wire threaded on external threads arranged on the outside of the valve housing.

Another preferred embodiment is characterised in that the increase of the diameter of the helix shaped wire at its upper end is more than 15%.

A preferred embodiment is characterised in that the increase of the diameter of the cylinder at its upper end is at least 40%.

Another preferred embodiment is characterised in that the increase of the diameter of the helix shaped wire at its upper end is at least 40%.

A preferred embodiment is characterised in that the increase of the diameter of the helix shaped wire at its upper end after expansion is at least 25%.

Another preferred embodiment is characterised in that the increase of the diameter of the helix shaped wire at its lower end is at least 10%.

A preferred embodiment is characterised in that the increase of the diameter of the helix shaped wire at its lower end after expansion is at least 20%.

A preferred embodiment is characterised in that said valve holder comprise an expandable element having the possibility to shrink upon removal of said valve housing, A preferred embodiment is characterised In that the total length of the assembly is less than the length of the female urethra where it is intended to be inserted.

Another preferred embodiment is characterised in that the total length of the valve is less than 60 mm.

Another preferred embodiment is characterised in that the total length of the valve assembly is between 5 to 40 mm, preferably 5–30 mm.

A preferred embodiment is characterised in that at least a part of the length of the valve body of said valve assembly has a bending stiffness higher than 0.0004 $Nm^2$ (Newton square meter).

Another preferred embodiment is characterised in that at least a part of the length of the valve body of said valve assembly has a bending stiffness higher than 0.0004 $Nm^2$ (Newton square meter) and that at least a part of the length of the valve body of said valve assembly has a bending stiffness lower than 0.05 $Nm^2$ (Newton square meter).

A preferred embodiment is characterised in that the part of the valve assembly with bending stiffness higher than 0.0004 $Nm^2$ (Newton square meter) is less than 80% of the length of the female urethra were it is intended to be inserted.

Another preferred embodiment is characterised in that the part of the valve assembly with bending stiffness higher than 0.0004 $Nm^2$.(Newton square meter) is less than 50 mm.

A preferred embodiment is characterised in that the part of the valve assembly with bending stiffness higher than 0.0004 $Nm^2$ (Newton square meter) is less than 40 mm.

Another preferred embodiment is characterised in that the part of the valve assembly with bending stiffness higher than 0.0004 $Nm^2$ (Newton square meter) is between 5 and 60 mm.

Another aspect of the invention encompasses a valve adapted to be positioned into a urethra and in a valve assembly according to claims 1–36, said valve for emptying a patient's urine collected within his bladder, comprising:

a tubular valve housing having an upper, lower, and central part and a channel therein;

a valve body situated at the lower part of the housing a valve seat situated below said valve body, said central part having at least one drainage hole extending through said tubular housing, said drainage hole located in the area between the upper end and the valve seat, said channel of the valve housing in communication with said drainage hole, said valve body being arranged to be moved in a longitudinal and being characterised in that the total length of the valve is less than 60 mm.

A further aspect of me invention relates to a valve adapted to be positioned into a urethra and in a valve assembly according to claims 1–36, said valve-for emptying a patient's urine collected within his bladder, comprising:

a tubular valve housing having an upper, lower, and central part and a channel therein; a valve body situated at the lower end of the housing and attached to a valve rod which in an opposite end thereof comprises a magnet accommodated in the upper portion of the valve;

a valve seat situated below said valve body, said central part having at least one drainage hole extending through said tubular housing, said drainage hole located in the area between the upper part and the valve seat, said channel of the valve housing in communication with said drainage hole, said valve body being arranged to be moved in a longitudinal direction by means of a part of the valve rod extending below said valve rod.

A preferred embodiment is characterised in that the valve housing comprises a magnetic controlled valve.

Another preferred embodiment is characterised in that the valve is electro-magnetically controlled A preferred embodiment is characterised in that the valve is mechanically controlled.

Another preferred embodiment is characterised in that valve is electro-magnetically or mechanically controlled independent of the pressure in the bladder to be emptied.

Another preferred embodiment is characterised in that the valve may be opened by means of a opening force being between 10 to 200 mN.

A preferred embodiment is characterised in that the valve may be opened by means of a opening force being between 20 to 100 mN.

Another preferred embodiment is characterised in that the valve is partly flexible, and partly rigid, whereby the rigid part is shorter than 50 mm.

Figure 1:
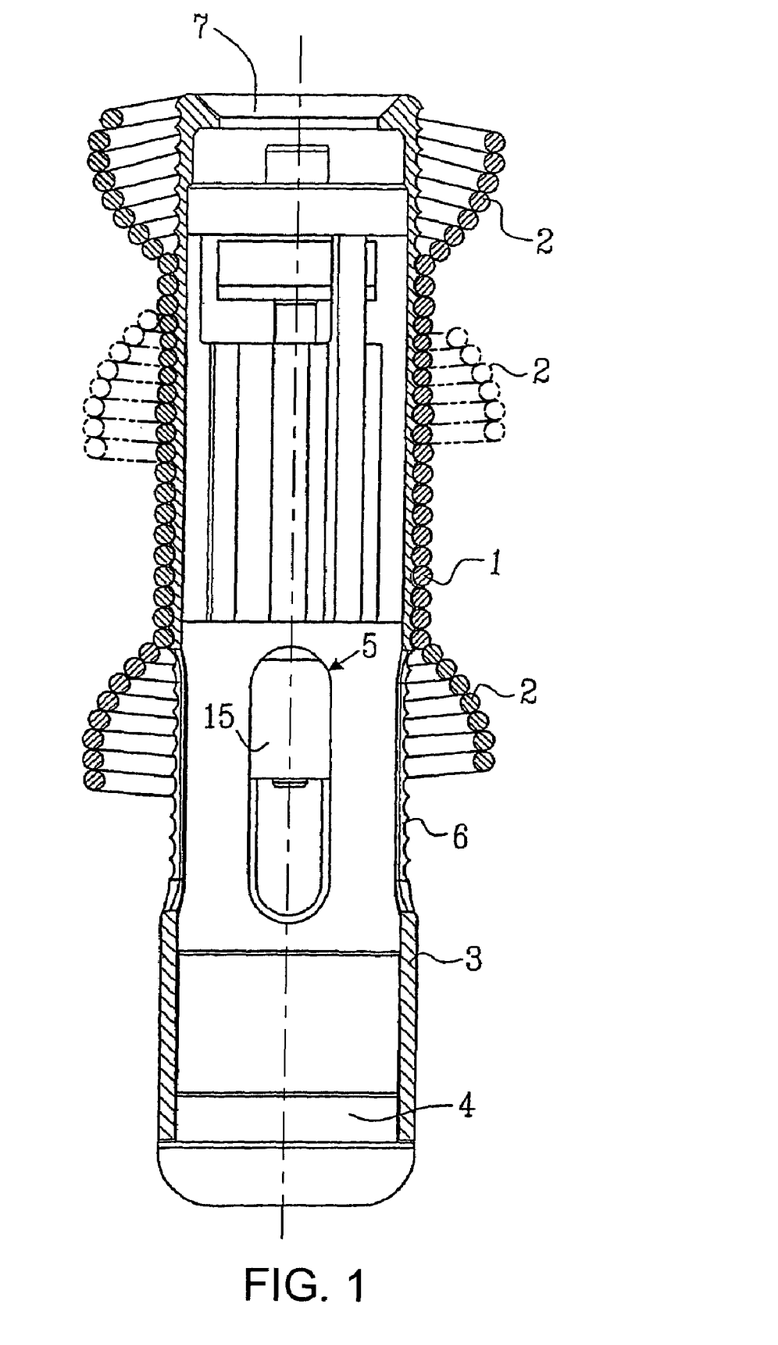
FIG. 1 illustrates schematically the valve holder of the present invention comprising a valve housing with its valve.

The invention will now be described with reference to the drawings indicated above. A valve holder 1 in accordance with the present invention, which is so arranged as to be positioned in an intended position in the urethra or in some other duct intended for emptying in a patient, either female or male, preferably at the upper part of the urethra, etc., in conjunction with the urine bladder on the inner side of the sphincter muscle of the urethra in the case of females, and the sphincter muscle and prostate in the case of males. The valve holder 1 is made of a memory metal alloy and is formed by a wire of said metal formed into a helix forming an open cylinder. When introducing the holder in the urethra the holder is cylindrical, but after insertion the metal is heated to some degrees centigrade above 40, whereby the proximal and distal ends thereof expand into frustoconical shape 2 and exert a pressure on the urethra wall to hold the holder in place. The metal is arranged to expand at least 10%, preferably at least 20% at its distal end, whereby the expansion of the central, cylindrical part should be less than 80%. In one embodiment the holder 1 is arranged to shrink onto the valve housing when subjected to a different temperature.

In the embodiment shown the holder 1 comprises opposite turned frustoconical ends. However, it is also possible to create a holder 1 comprising at least two frustoconical parts facing the same way. However, it is an advantage having the inner, proximal end opening inwards to the bladder.

Into the valve holder 1 a cylindrical valve housing 3 is positioned, which housing comprises a threaded outer surface being configured with the helix of the holder 1. For controlling purposes the essential length of the housing 3 is placed within the helix cylinder of the holder 1. The length of the total valve assembly is 5 to 40 mm, but can extend up to 60-mm length.

Figure 2:
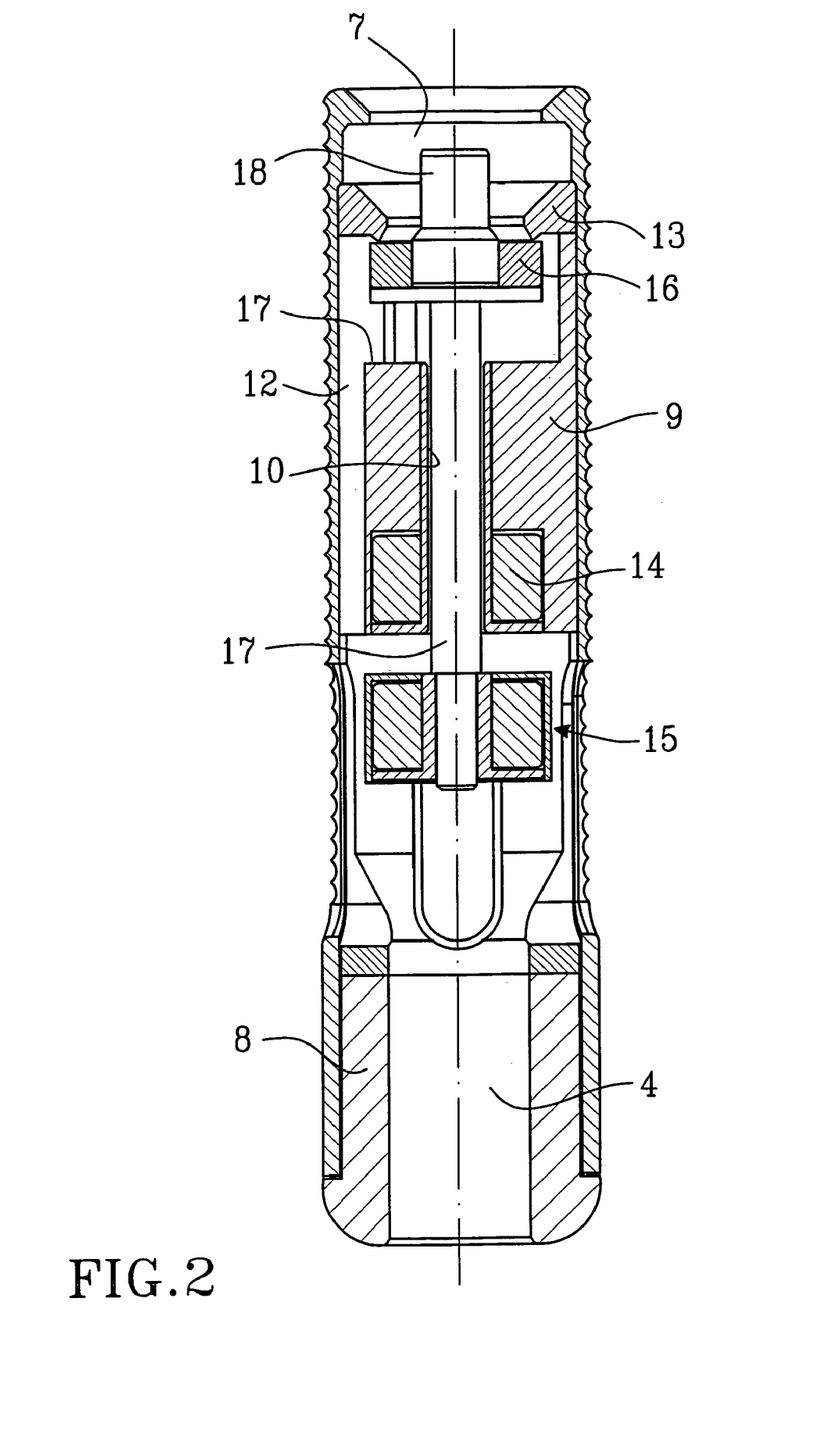
FIG. 2 shows a valve housing with its valve in closed position.
Figure 3:
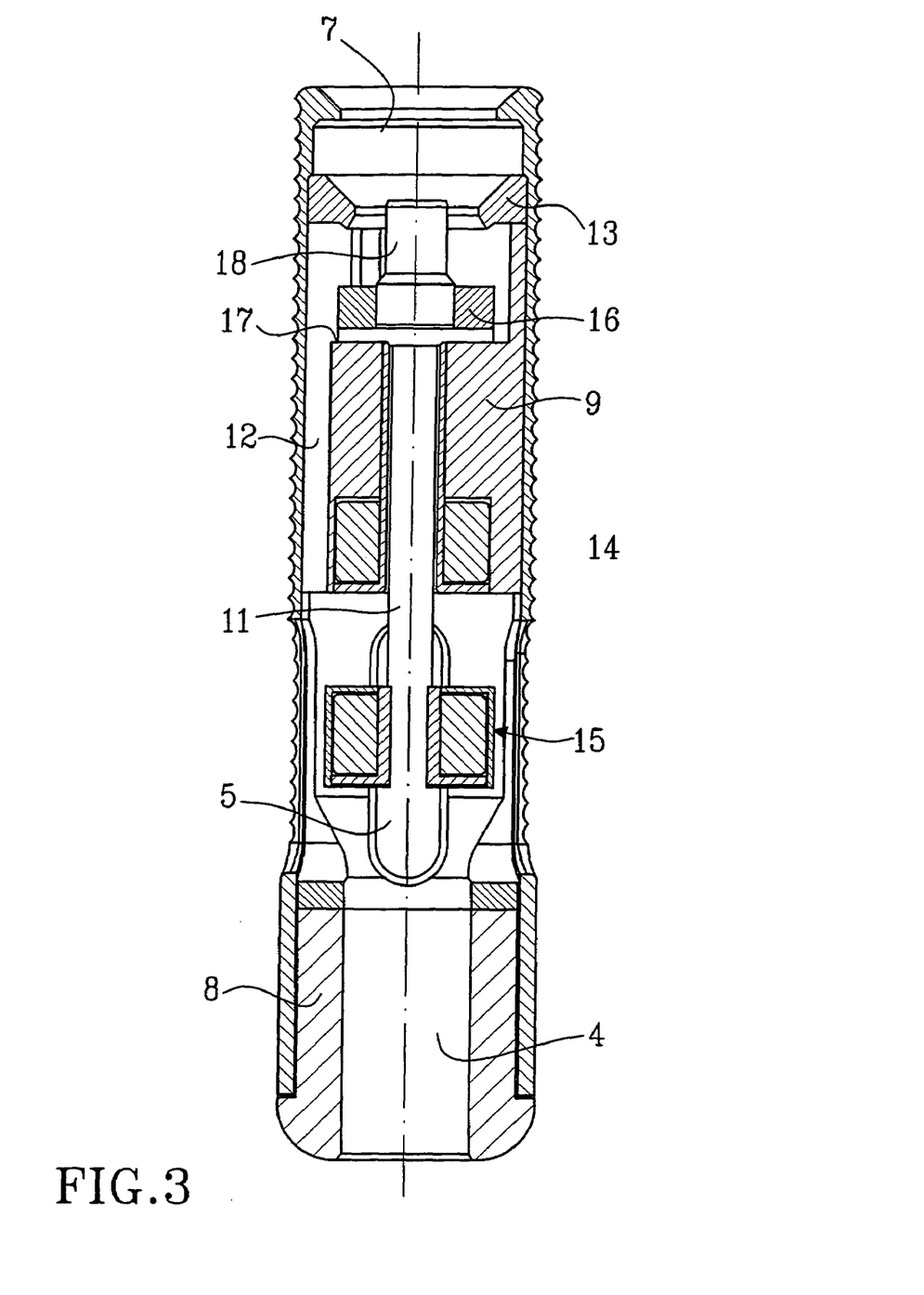
FIG. 3 shows a valve housing with its valve in open position.

The valve housing 3 exhibits generally a number of openings to allow a flow of liquid therethrough and those openings are, in the embodiment shown, an axial inlet opening 4 at the proximal end, and four lateral inlet openings 5 extending through the housing wall 6 and placed generally in the centre part of the housing, as well as a distal axial outlet opening 7. FIGS. 2 and 3 shows the valve housing and its valve more in detail. As evident from the drawing the housing, in the embodiment shown, is threaded from the distal end and two thirds of the length, approximately to the site of the side openings 5. Inside the valve housing 3 at the proximal end there is general stopper 8 provided with a through-going, axial hole 4. The valve housing further comprises a valve body 9 provided with a central through-opening 10 to accommodate a valve rod 11, and a peripheral, axially extending flow opening 12, At the distal end of the valve there is a valve seat 13 provided which leads out to the distal outlet opening 7, The valve body 9 accommodates a permanent or electro-magnet 14 surrounding the central axial opening 10. Said opening 10 accommodates the valve rod 11 which at its proximal end receives a permanent or electro-magnet 15, and at its distal end receives a valve 16 arranged to be placed against the valve seat 13. The valve rod 13 extends through the valve as such and exhibits a distal part 18 arranged to be actuated, either manually or mechanically.

Figure 4:
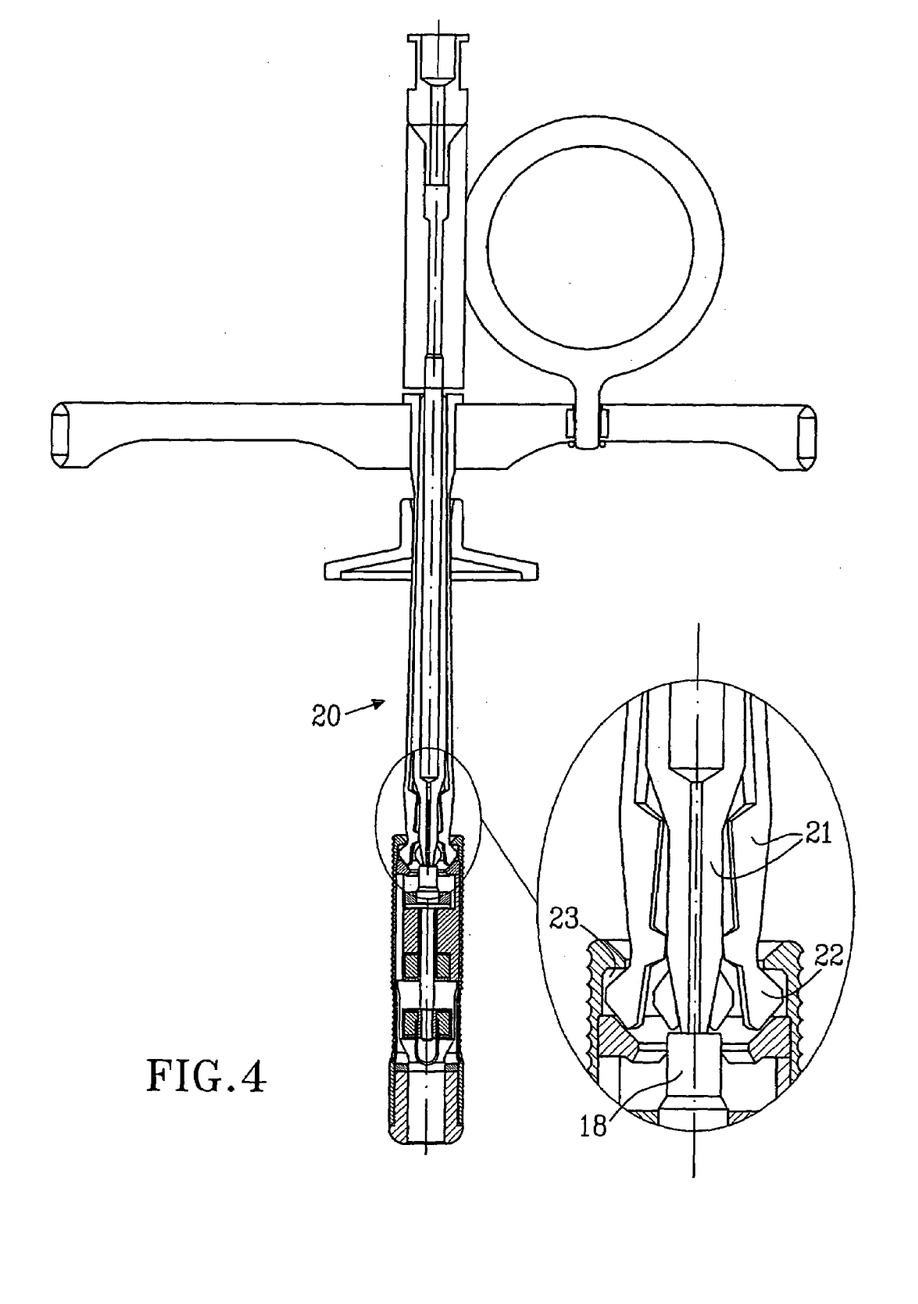
FIG. 4 shows an aid tool for applying the valve assembly and/or applying/removing the valve housing with its valve.

The valve assembly is so arranged as to be positioned simply and without pain in the urethra etc., and to be regulated externally by the patient. More specifically, the entire valve assembly is so arranged as to be capable of being positioned in the urethra, etc., in its internal space and of being removed from it with the help of a tool 20 intended for that purpose capable of being accommodated inside the urethra, etc,, and activated from the outside of the patient's body. The valve assembly in accordance with the invention is also adjustable from the outside of the patient's body to permit emptying or the urine bladder, etc. The Valve assembly shall be positioned at least 10 mm from the distal opening end of the urethra, and should be positioned 10 to 150 mm from said opening depending on female or male urethra positioning.

The valve may, as shown in drawings such as FIGS. 2–3, be of a mechanical kind with a valve 16 accommodated in such a way as to be capable of movement inside the cylindrical valve housing 3, which valve body preferably consists of a permanent magnet, in conjunction with which a stop 17 is situated in the distal facing part of the valve body 9.

Also present are a number of drainage holes 5 extending preferably perpendicularly through the wall of the valve housing 3. Said drainage holes 5 extend through the tubular outer casing of the valve housing as far as to an internal cavity in the central part of the valve housing and the transcurrent axial channel 12 of the valve housing, for the purpose of emptying urine, etc., through the valve with the valve pushed into its inserted position, and of connecting the outlet of the valve when it's rod is in its proximal position, and the connected drainage holes 5 and channel 12.

The valve seat 13 is accommodated internally in the valve body 9 and interacts with the valve 16. The valve seat 13 is constructed preferably as a sleeve together with an appropriate and matching seal.

At least a part of the length of the valve body of said valve assembly has a bending stiffness higher than 0.0004 $Nm^2$ (Newton square meter), whereby preferably at least a part of the length of the valve body of said valve assembly has a bending stiffness higher than 0.0004 $Nm^2$ (Newton square meter) and that at least a part of the length of the valve body of said valve assembly has a bending stiffness lower than 0.05 $Nm^2$ (Newton square meter), and whereby the part of the valve assembly with bending stiffness higher than 0.0004 $Nm^2$ (Newton square meter) is less than 80% of the length of the female urethra where it is intended to be inserted, whereby the part of the valve assembly with bending stiffness higher than 0.0004 $Nm^2$ (Newton square meter) is less than 50 mm, preferably the part of the valve assembly with bending stiffness higher than 0.0004 $Nm^2$ (Newton square meter) is less than 40 mm, and preferably the part of the valve assembly with bending stiffness higher than 0.0004 $Nm^2$ (Newton square meter) is between 5 and 60 mm. The total length of the assembly is less than the length of the female urethra where it is intended to be inserted, preferably the total length of the assembly is less than 80% of the female urethra were it is intended to be inserted.

Said valve is capable of manual actuation. For the purpose of emptying the urine bladder, the valve 16 must be moved mechanically with the help of the actuating device 18, actuated by such as a catheter, a probe, a wire, or a C-shaped piece of tubing, capable of being introduced from the outside through the urethra as far as the valve.

The valve assembly must be capable of being positioned by a simple cystoscopy procedure, which, in adult patients, does not even require general anaesthesia and should be performed under a local anaesthetic. Given the right surface treatment, the valve should be capable of remaining in place for at least six months, and perhaps longer, before it needs replacement. With the design of the valve described here, removal and insertion of a new valve should also be a simple procedure. The medical advance lies essentially in the fact that the alternative for that group of patients with a weak urethra sphincter muscle is major surgery, the outcome of which, as already mentioned, is not always satisfactory. Many patients with a dysfunctional sphincter muscle are already being advised to insert a catheter into the urine bladder at regular intervals; this is known as Clean Intermittent Catheterization (CIC). For these individuals, it is sufficient to have a valve with a permanent magnet that is opened by introducing a catheter or a probe into the urethra. In most cases, however, it is desirable to have a valve with an electromagnet capable of being opened by transcutaneous induction to a coil positioned in the subcutaneous fat layer, thereby dispensing with the need to introduce a catheter into the urethra. For previously severely incontinent persons, who are able in this way to control their urethra in a totally non-invasive fashion, the valve would represent an enormous increase in their quality of life. The valve body, which, like the valve head 15, preferably consists of a permanent magnet, is always in the closed position if it is mechanically inactivated externally. This is made possible thanks to the force with which the magnet is pulled against the distal end.

Said valve assembly, which is positioned in the inner upper part of the urethra, can thus be regarded as replacing a damaged or dysfunctional sphincter muscle for a urethra.

The valve housing and the stop can be made of bronze or titanium, and the valve body and the valve head can comprise permanent magnets, whilst the seal can consist of a glued-on sheet of silicone rubber of the desired thickness. The sealing should have a Shure value of 20 to 50, preferably 35 to 45. All components other than the seal are coated with a nickel anti-corrosion treatment, which also serves as the base for subsequent plating with gold, which is inert, is not rejected by the tissues, and does not provide a point of attachment for urine crystals and bacteria. The application of such a valve in the right situation/position in a patient is possible by causing the valve to be introduced through the urethra from its external opening with the help of a combined application/removal tool 20, for example of the kind illustrated in the drawings in FIG. 4. An expandable head 21 situated at the front, which can exhibit externally devices 22 that are capable of interacting with internally devices 23 on the distal end part of the valve to permit them to be securely screwed together, forms a guide component and a means of attachment to the valve. When the valve, after having been securely screwed to the tool 20, has been introduced through the opening of the urethra to the desired extent, which can be verified using ultrasound or x-rays, etc., the head 21 is unscrewed with the help of a rear handle, for example on a flexible cable, and is withdrawn from the urethra.

The valve, which can be made in different sizes to suit the urethra and the incontinence problem of the individual patient, must be replaced at intervals of approximately six months. An electrically actuated valve permits actuation of the valve from outside the patient's body without the need for the introduction through the urethra of any long devices to effect emptying. The valve is then so arranged as to be opened or closed by means of electrical impulses through so-called remote control. Present inside a cylindrical valve housing at the rear end of the valve is an internal axial central passageway, and present around said valve seat, which is formed by a magnetic core, is a magnetic winding, which exerts a pulling force to close the valve, and a further magnetic winding, which exerts a pushing force in the opposite direction to open the valve in the area of the centre of the valve. Similarly present at the front end of the valve are magnetic windings, which respectively exert a pushing force and a pulling force for the purpose respectively of closing and opening the valve.

When the valve assembly is positioned in the upper part of an urethra, said drainage hole 4 is situated inside the bladder and the drainage holes 5 are situated inside the frustoconical art of the holder 1, whereas the external attachment parts of the holder are attached to the urethra on its inside.

The permanent magnets are preferably in equilibrium, so that a relatively small polarity reversal impulse, or push force, such as 10 to 200 mN, causes the valve respectively to open and close. The use of a magnet, either permanent or electro-driven, is an advantage over having a spring-biased valve construction as the force to open the valve will become smaller as the magnet is removed, contrary to the situation having a spring-biased valve where the force becomes larger the more the spring is removed from its neutral position, either compressed or extended.

The valve, which is intended to be replaced at regular intervals, for example every sixth month, by external influence, is so arranged as to be capable of being ejected automatically from the urethra, etc., if excessive pressure builds up inside the urine bladder, etc., for example is the valve opening process is impeded. There is accordingly no security risk, thanks to the safety function whereby the valve is able to leave the patient's body, which function is effective independently of the valve function.

The electrical valve must satisfy the above criteria, apart from the possibility that insertion/removal of the electrical control means of the valve may require a minor surgical operation. The invention is not restricted to the. illustrative embodiments described above and illustrated in the drawings, but may be modified within the scope of the claims without departing from the idea of invention.

The invention claimed is:

1. A valve assembly adapted to be positioned into a urethra in a mammal, including humans, the valve assembly comprising:
    a) a valve holder comprising a substantially cylindrically shaped body to be inserted into the urethra, and
    b) a valve housing comprising a valve controlling an urine flow from a patients bladder, the valve assembly adapted to be arranged in a sealed manner between the walls of the urethra,
    wherein the cylindrical valve holder comprises a shape memory alloy to provide an expandable element adapted to expand after the insertion of said valve holder to increase its diameter at its upper end to provide a frustoconical portion, whereby the increase of the diameter of the cylinder at its upper end is more than 15% and whereby the increase of the diameter of said cylindrical valve holder is temperature dependent; and
    wherein the valve holder comprises at least two frustoconically shaped portions at one end of the cylinder corresponding to said frustoconical portion.

2. A valve assembly according to claim 1, wherein the cylindrical valve holder increase its diameter at its lower end.

3. A valve assembly according to claim 1, wherein the valve holder comprises said at least two frustoconically shaped portions at one end of the cylinder as well as at least one frustoconically shaped portion at the opposite end thereof, both of which correspond to said frustoconical portion.

4. A valve assembly according to claim 3, wherein the valve holder includes a first portion corresponding to said at least two frustoconically shaped portions at one end of the cylinder, a second portion being essentially cylindrical and a third portion corresponding to said at least one frustoconically shaped portion at the opposite end and directed in opposite direction in relation to the first portion.

5. A valve holder according to claim 1, wherein the holder and the housing are detachable from each other when in place in the urethra.

6. A valve assembly according to claim 1, wherein the holder and the housing are detachable from each other.

7. A valve assembly according to claim 1, wherein the holder is helix shaped wire arranged onto the valve housing.

8. A valve assembly according to claim 1, wherein the holder comprises a helix shaped wire threaded on external threads arranged on the outside of the valve housing.

9. A valve assembly according to claim 8, wherein the increase of the diameter of a helix shaped wire at its upper end is more than 15%.

10. A valve assembly according to claim 9, wherein the increase of the diameter of a helix shaped wire at its upper end is at least 40%.

11. A valve assembly according to claim 9, wherein the increase of the diameter of a helix shaped wire at its upper end after expansion is at least 25%.

12. A valve assembly according to claim 9, wherein the increase of the diameter of a helix shaped wire at its lower end is at least 10%.

13. A valve assembly according to claim 9, wherein the increase of the diameter of a helix shaped wire at its lower end after expansion is at least 20%.

14. A valve assembly according to claim 8, wherein the increase of the diameter of the cylinder at its upper end is at least 40%.

15. A valve assembly according to claim 1, wherein the increase of the diameter of the cylindrical portion of the valve holder is less than 80%.

16. A valve assembly according to claim 1, wherein said valve holder comprise an expandable element having the possibility to shrink upon removal of said valve housing.

17. A valve assembly according to claim 1, wherein the total length of the assembly is less than the length of the female urethra where it is intended to be inserted.

18. A valve assembly according to claim 1, wherein the total length of the valve is less than 60 mm.

19. A valve assembly according to claim 1, wherein the total length of the valve assembly is between 5 and 40 mm, preferably 5–30 mm.

20. A valve assembly according to claim 1, wherein at least a part of the length of the valve body of said valve assembly has a bending stiffness higher than $0.0004\ Nm^2$ (Newton square meter).

21. A valve assembly according to claim 1, wherein at least a part of the length of the valve body of said valve assembly has a bending stiffness higher than $0.0004\ Nm^2$ (Newton square meter) and that at least a part of the length of the valve body of said valve assembly has a bending stiffness lower than $0.05\ Nm^2$ (Newton square meter).

22. A valve assembly according to claim 1, wherein the part of the valve assembly with bending stiffness higher than $0.0004\ Nm^2$ (Newton square meter) is less than 80% of the length of the female urethra where it is intended to be inserted.

23. A valve assembly according to claim 1, wherein the part of the valve assembly with bending stiffness higher than $0.0004\ Nm^2$ (Newton square meter) is less than 50 mm.

24. A valve assembly according to claim 1, wherein the part of the valve assembly with bending stiffness higher than $0.0004\ Nm^2$ (Newton square meter) is less than 40 mm.

25. A valve assembly according to claim 1, wherein the part of the valve assembly with bending stiffness higher than $0.0004\ Nm^2$ (Newton square meter) is between 5 and 60 mm.

26. A valve according to claim 1,
wherein the valve is mechanically controlled.

27. A valve according to claim 1,
wherein the valve is electro-magnetically or mechanically controlled independent of the pressure in the bladder to be emptied.

28. A valve according to claim 1,
wherein the valve may be opened by means of an opening force being between 10 to 200 mN.

29. A valve according to claim 28, wherein the valve may be opened by means of a opening force being between 20 to 100 mN.

30. A valve according to claim 1, wherein the valve is partly flexible, and partly rigid, whereby the rigid part is shorter than 50 mm.

31. A method for emptying a patient's urine bladder, whereby the valve assembly in accordance with claim 1 is inserted in the urethra and influenced at time intervals to open and empty said bladder.

* * * * *